United States Patent [19]

Puffer

[11] Patent Number: 4,563,095
[45] Date of Patent: Jan. 7, 1986

[54] METHOD AND APPARATUS FOR MONITORING THE SURFACE OF ELONGATED OBJECTS

[75] Inventor: LeRoy G. Puffer, Vernon, Conn.

[73] Assignee: Essex Group, Inc., Fort Wayne, Ind.

[21] Appl. No.: 451,632

[22] Filed: Dec. 20, 1982

[51] Int. Cl.[4] .......................................... G01N 21/32
[52] U.S. Cl. .................................... 356/430; 356/237; 356/446; 250/562; 250/572
[58] Field of Search ............... 356/237, 445, 429, 446, 356/430, 431; 250/562, 563, 572; 118/670, 688, 712

[56] References Cited

U.S. PATENT DOCUMENTS

| 3,399,592 | 9/1968 | Brachvogel et al. | 356/237 |
| 3,588,513 | 6/1971 | Akamatsu et al. | 356/430 |
| 3,992,111 | 11/1976 | Roulier et al. | 356/431 |
| 4,095,905 | 6/1978 | Kuni et al. | 356/446 |
| 4,184,770 | 1/1980 | Pinior | 356/430 |
| 4,305,661 | 12/1981 | Pryor et al. | 250/563 |
| 4,358,202 | 11/1982 | Puffer et al. | 356/430 |
| 4,468,120 | 8/1984 | Tanimoto et al. | 250/563 |

FOREIGN PATENT DOCUMENTS 880135 10/1961 United Kingdom ............... 356/431

Primary Examiner—R. A. Rosenberger
Attorney, Agent, or Firm—Stephen A. Schneeberger

[57] ABSTRACT

A method and apparatus for monitoring the surface of an elongated, normally-smooth object, such as coated cable, for certain flaws. The object is longitudinally movable along a path. Radiation, such as white light, is directed at the object such that it is incident therewith throughout a narrow zone extending substantially entirely around the object's perimeter. The angle of incidence of the light with the object is such that a normally smooth surface specularly reflects light at a relatively large angle, whereas particular flaws, such as pips and the like, scatter the light in a particular direction longitudinally of the object and at a relatively smaller or limited angle thereto. A slotted mirror is disposed concentrically about the object's path and reflects the scattered light to imaging and detecting devices, such as a charge injection device. Analytical electronics connected to the detector analyze its electrical signal to indicate the presence of a flaw. The electronics may include a counter for size-quantifying the image on the detector, as a condition to indicating the existence of a flaw.

13 Claims, 5 Drawing Figures

METHOD AND APPARATUS FOR MONITORING THE SURFACE OF ELONGATED OBJECTS

DESCRIPTION

1. Technical Field

This invention relates to method and apparatus for monitoring the surface of an object, and more specifically relates to an optical system for monitoring the surface characteristics of elongated objects, such as the surface of cables or coatings thereon.

2. Background Art

As part of the process associated with the manufacture of various elongated objects, it is frequently desirable to inspect or continuously monitor the product at one or more stages in its manufacture to assure conformity to design and manufacturing standards and/or to identify certain departures from those standards. One parameter frequently of concern in the manufacture of elongated products such as electrical cable is that of surface character or texture. For instance, high voltage electrical cable conventionally consists of one or more center conductors surrounded by a semiconductive material in turn surrounded by an insulator. The semiconductive material is applied to the center conductor by an extrusion process. It is important that the outer surface of this semiconductive coating be smooth, inasmuch as various flaws or irregularities, and particularly those relatively abrupt discontinuities known as "pips", in the surface of the semiconductive coating can result in in-service cable failure requiring costly repair or replacement. Other surface flaws which occasionally warrant detection include "flat-faced" flaws and "bulges". Therefore, it is desirable during or after manufacture to be able to detect different types of such irregularities in the cable coating surface anywhere about its periphery and along its length, and take appropriate corrective or preventative measures.

It is generally preferable to monitor the product, i.e. coated cable, on line during its manufacture. For that reason, it is preferable to have a noncontact monitoring process which does not inhibit the speed of the manufacturing process nor require the product surface being monitored to be hard and durable at that time. Electrooptical techniques are especially well suited to such monitoring requirements.

Some systems for monitoring the surface character and geometry of elongated products, such as electrical wires and cables, position a light source on one side of the cable and a detector on the opposite side to develop a shadow profile of the cable. This, of course, limits the amount of the cable which can be seen unless a plurality of light sources and detectors is employed. Another system projects or scans a beam of light across the width of a moving member to be inspected, and a sensor positioned on the same side of the member detects light reflected by various irregularities in the member surface. However, that system views only the side of the member facing the light scanner and sensor, and is best suited for monitoring flat rather than curved surfaces.

A recent U.S. patent application Ser. No. 172,738 filed July 28, 1980, now U.S. Pat. No. 4,358,202 by Puffer et al for Apparatus and Method for Monitoring the Surface Character of Circular Objects, and assigned to the assignee of the present application, discloses a system which overcomes many of the various shortcomings of the aforementioned prior art. That system develops a beam which orbits the path of the cable and is directed into incidence with the surface of the cable at an angle substantially normal thereto. The beam is specularly reflected by the surface of the cable back over substantially the same angle at which it was incident and is then brought to focus for collection by an appropriate detector. Although that system has the ability to examine the full surface circumference of the coating on a long continuous cable, various common surface characteristics may cause undesirable noise in the detected signal. More specifically, that system detects most of the light specularly reflected from the surface of the cable when that surface is smooth and any of a variety of irregularities in that surface tend to diminish the light energy sensed by the detector and are thus considered to be "pips". If the cable is formed of several wound conductors, the coating may develop helical ridges known as "rope". Further, if the cable is relatively small, it may develop bends or "kinks" due to winding and unwinding in its formation. Neither the "rope" nor the "kink" characteristics are particularly objectionable from the standpoint of the integrity of the insulative coating, but they are the types of irregularity which may cause undesirable noise in the detected signal.

Accordingly, while it is important for such a surface-monitoring system to be capable of accurately detecting surface flaws such as "pips", such system should discriminate from the other acceptable characteristics such as "rope" and "kinks". Moreover it may be desirable for the surface monitoring system to be capable, either alternatively or concurrently, of detecting different types of such flaws. Additionally, the optics of such system should permit inspection of the entire cable circumference with a minimum of moving parts and other optical components. Further, the optics of such system should be designed and arranged to facilitate rapid installation about and removal from a cable in a manufacturing environment.

In accordance with the present invention, there is provided a method and apparatus for monitoring the surface of an elongated, generally circular object, such as a coating surface on an electrical cable. A thin annular zone of the coated surface of the cable is irradiated by electromagnetic energy directed so as to be incident therewith at a selected angle, typically normal thereto in one embodiment. The electromagnetic energy may be white light or it may be coherent light from a laser, and may derive from one or several sources of such radiant energy. A mirror is positioned in general proximity with the cable under inspection at a location which is longitudinally displaced from that portion of the cable surface which is irradiated. That mirror may be formed and positioned in a manner such that it is substantially concentric with the cable, and the cable moves relative to both the mirror and the band of irradiation. The mirror is preferably of U-shaped form for easy relative insertion and removal of the cable within the slot thereof. If the surface of the cable coating is smooth or includes only "rope" and/or "kinks", the radiation incident thereon is normally specularly reflected therefrom, as for instance back over substantially the path of incidence if normal to the surface. On the other hand, relatively abrupt discontinuities such as "pips" on the surface of the cable coating will serve to scatter the radiation in various directions, including longitudinally (axially) of the cable. A portion of the radiant energy scattered longitudinally of the cable will be incident on the mirror and is then deflected through suitable optics, such as an imaging lens for imaging onto a detector array. The detector array is preferably of a type possessing anti-blooming characteristics, such as a charge injection device (CID), and provides an electrical signal suitable for electronic analysis of the image so formed thereon. Further, utilization electronics may respond to the detector's electrical signal to generally indicate characteristics of the cable coating surface, including presence or absence of "pips" of at least a certain size.

In the event it is desired to detect "flat-faced" flaws having a face which is substantially normal to the surface of the cable, the angle of incidence of the light may be selected such that only light scattered from that face is received at the mirror. On the other hand, if it is desired to detect "bulge" type flaws having a more gradual slope than either "pips" or "flat-faced" flaws, the angle of incidence of the light may be selected to be in the same general direction as the mirror, but at an angle such that only light scattered by the bulge is received at the mirror.

BEST MODE FOR CARRYING OUT THE INVENTION

Figure 1:
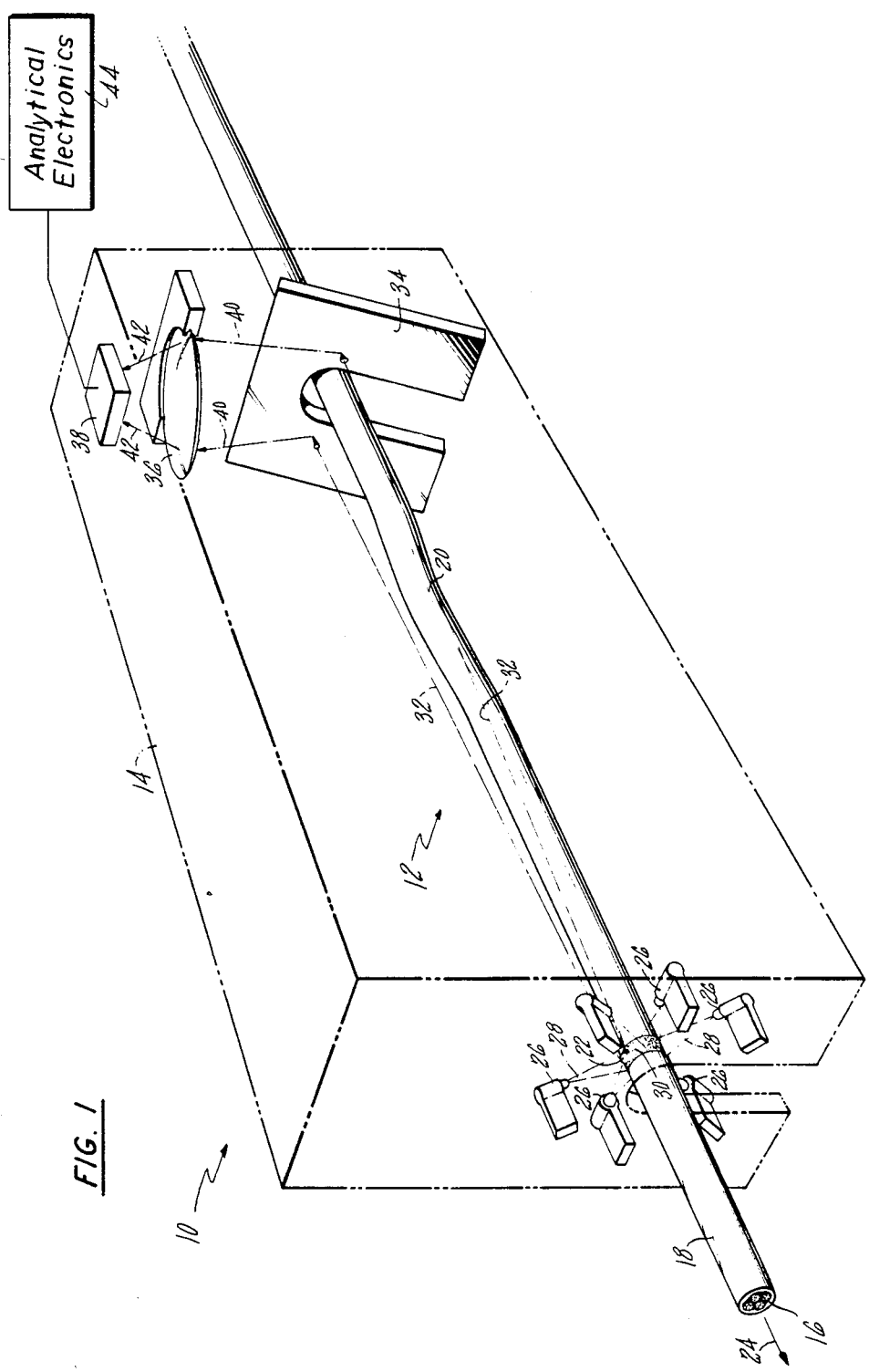
FIG. 1 is a simplified schematic view of an actual optical system in accordance with the monitor of the present invention.

Referring to FIG. 1 there is illustrated a cable coating monitor 10 in accordance with the invention. The monitor 10 includes an optical system, generally designated 12, mounted in and protectively housed by a hood 14 (shown in broken lines). The hood 14 typically includes a longitudinal opening at its bottom which extends upwardly at each end to facilitate installation and removal of the monitor 10 about a continuous length of coated cable 16.

The cable 16 may typically be of the type designed for the conduction of high electrical voltages and will include a single or multi-strand metal center conductor and an overlying semiconductive coating formed thereon prior to the formation thereover of a tubular insulating covering. The semiconductive coating is generally formed over the center conductor by means of an extrusion process. The outer surface of that semiconductive coating is preferably smooth, however, it may occasionally possess some low helical ridges known as "rope" 18, and/or some shallow bends known as "kinks" 20, and/or some relatively large amplitude irregularities or discontinuities such as "pips" 22. While neither the "rope" nor the "kinks" are considered particularly objectionable, the so-called "pips" 22 are flaws which may give rise to certain voltage breakdown and corona phenomena which can prove damaging to the cable. As used herein, a "pip" is the term given to discontinuities in the cable surface which may be about 1–10 mils more or less in height and 5–40 mils more or less in length or width. A "pip" typically has a slope which is fairly steep, but not normal to, the surface of the cable, as shown more clearly in FIG. 3. It is preferable to detect such "pips" 22 prior to application of the insulating coating to allow necessary remedial action.

The semiconductor-coated cable 16 is substantially continuous and is caused to move along a path represented by arrow 24. The path 24 includes a linear region of sufficient length to accommodate the positioning of housing 14 and the associated optics 12 thereover. The optics 12 include a source of electromagnetic radiation or light for directing a plane or zone of light onto the surface of cable 16 substantially normal thereto and about substantially the full circumference thereof.

More specifically, in the illustrated embodiment a plurality of white light sources 26 are mounted on the interior of housing 14 and arranged in equiangularly spaced relation about the cable path 24. Each light source 26 projects a beam of light 28 such that it is incident with the surface of cable 16 at an angle substantially normal thereto. Moreover, the number of white light sources 28 and the angular disperion of their respective light beams 28 cumulatively is such that an annular line or band 30 of the surface of cable 16 is irradiated by the light. In the illustrated embodiment there are six sources 26 of white light and the spread of the resulting beams 28 irradiates an annular band 30 having a significant width, i.e. 1–5 mm. It will be appreciated that instead of the plural white light sources 26, a single beam of coherent radiation from a laser may be passed through a cylindrical expanding lens to produce a wide plane of light, which plane of light may then be deflected by a plurality of mirrors such that it is incident with the surface of cable 16 along most or all of an annular line 30 about the cable.

Figure 3:
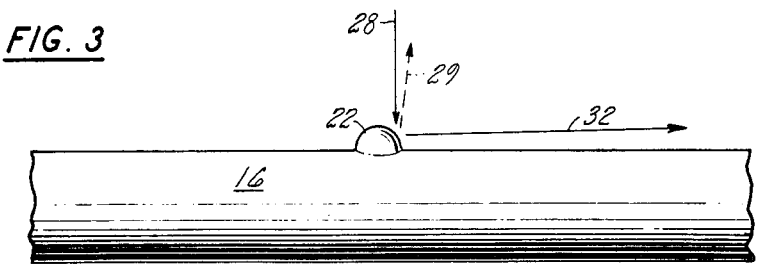
FIG. 3 is an enlarged diagrammatical view showing irradiation of the "pip" type of flaw on the cable surface.

Assuming the surface of cable 16 is relatively smooth, the light incident normal thereto about band or line 30 is specularly reflected back in substantially the same direction, as represented by the broken line 29 in FIG. 3. Stated another way, the specularly reflected light will be directed away from the cable 16 at a large angle which is nearly normal (i.e. 70°–90°) to the travel path 24 of the cable. In the event the surface of cble 16 possesses either "rope" 18 or "kink" 20, that angle of specular reflection may deviate somewhat more from that for a smooth cable surface, yet it still is at a relatively large angle (i.e. 45°–90°).

On the other hand, when the "pip" 22 appears in the irradiated band 30, the incident light will be scattered in numerous directions. Because of the characteristic abruptness or relatively steep slope to the "pips" 22, a significant portion of the light is scattered in a longitudinal direction back along cable 16 at a relatively small angle (i.e. 0°–30°) thereto, as represented by the lines 32. Collecting optics include a deflecting mirror 34 and an imaging lens 36 for respectively collecting the light scattered longitudinally of the cable 16 and imaging that deflected light onto an antiblooming detector array 38. The mirror 34 is configured and positioned such that it provides a reflecting surface which surrounds most of cable 16 in relatively close proximity therewith such that the scattered light 32 directed generally along cable 16 is in a zone occupied by the mirror and is thus incident with the mirror and is redirected off-axis to the imaging lens 36 which then images the scattered light on the active surface of detector array 38.

The mirror 34 is conveniently a single U-shaped mirror which receives the cable 16 in the slot between the adjacent legs of the "U". The slot in mirror 34 extends to the side of cable 16 which is opposite to the direction in which light is reflected from the mirror toward detector 38 via imaging lens 36, because the cable would shadow reflections from that location even if the slot weren't there. Further, it is desirable that the slot extends upward from the lower edge of mirror 34 to allow the cable 16 to droop or to fall free without contacting the optics, in the event cable tension is released. Thus, the housing 14, and the mirror 34 therein, are operatively positioned over cable 16 by downward displacement of the housing.

Because the present invention relies upon the collection of diverging light scattered generally longitudinally of cable 16 for indicating the presence of a "pip" 22 and the anti-blooming detector array 38 is not sensitive to small fluctuations of image brightness, the relatively small discontinuity in the surface of the mirror occasioned by the presence of the slot has relatively little effect on the collection of such scattered light. However, it has been found desirable to increase the illumination intensity of the two lower white light sources 26, as by increasing their supply voltage, to compensate for the small loss of light occasioned by the mirror discontinuity. This insures that sufficient scattered light will be collected to provide the requisite image brightness for "pips" located on the bottom of cable 16.

The scattered light 32 incident upon mirror 34 is then deflected, as represented by lines 40, to the imaging lens 36. The imaging lens 36 collects the scattered light received from mirror 34 and focuses it, as represented by lines 42, upon the surface of detector 38. The detector array 38 is preferably of the type possessing anti-blooming characteristics, such as a charge injection device (CID), having an array or matrix defining a large number of discrete picture elements, or pixels, for maintaining the fidelity of the image projected thereon. One suitable CID detector array 38 employs an orthogonal grid of 248 pixels by 244 pixels. The detector 38 is operatively connected to suitable analytical electronics, represented by the function block 44, for scanning the detector array 38 and providing the necessary logic and/or display functions.

Generally speaking, the detector 38 receives a relatively low level of scattered light if the coating of cable 16 is smooth or relatively so. However, when a "pip" 22 passes through the band 30 of irradiation, it scatters a significantly greater amount of light longitudinally of cable 16 onto mirror 34 and ultimately appears as a focused image on the detector 38. Firstly, the level of light in that image occasioned by pip 22 will be substantially greater than is otherwise the case, and secondly, the focused image corresponds with and is representative of the cross-sectional size and shape of the pip observed in a general axial direction.

Figure 2:
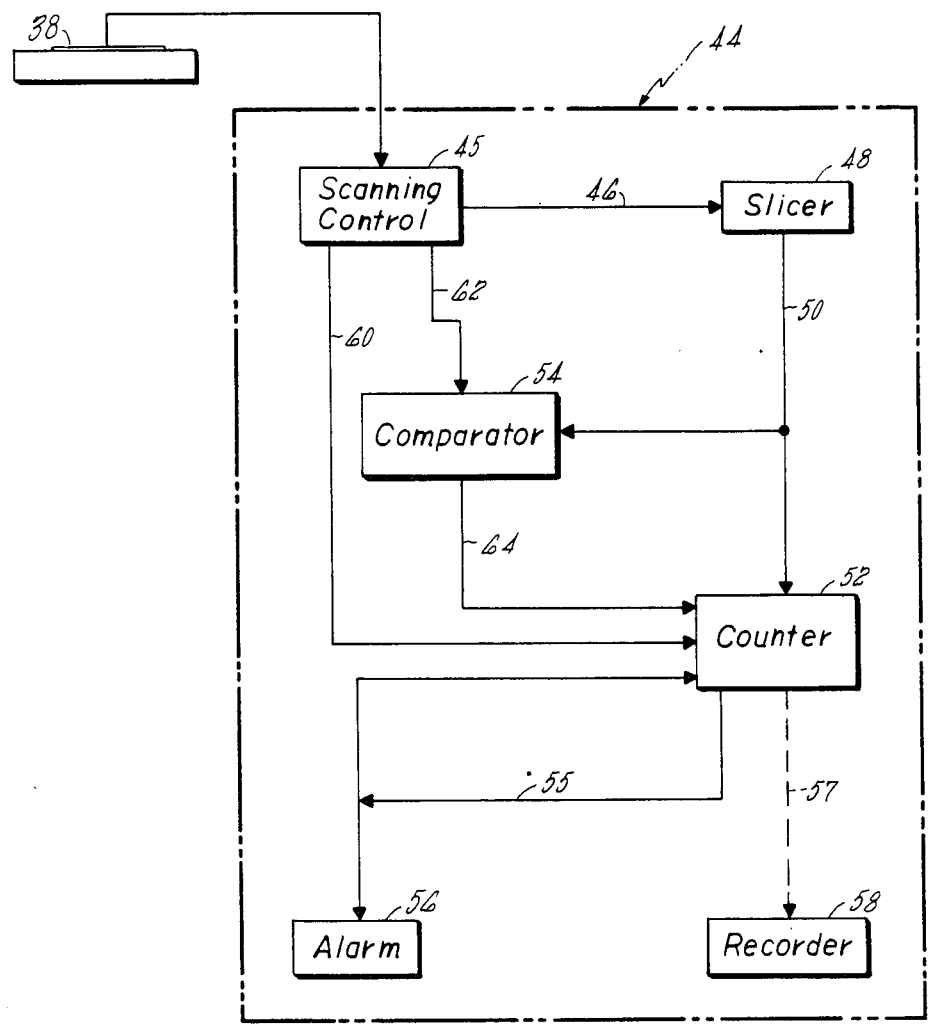
FIG. 2 is a functional block diagram of the analytical electronics of the invention.

Referring to the analytical electronics 44 as functionally depicted in FIG. 2, scanning control electronics 45 provide a scanning raster for scanning the pixel outputs of detector 38. The scanned signal from detector 38 is extended, as represented by line 46, to slicer 48 which provides an output only if the intensity of the light signal for a respective pixel exceeds a threshold which is preselected to reject low-level light from acceptable cable surface. The output of slicer 48 is extended as represented by line 50, to a counter 52 and a comparator 54. The counter 52 increments each time a pixel senses light above the threshold level, and provides an output 55 to an annunciator or alarm 56 each time is preselected count (i.e. 16) is reached. The count selected is one indicative of a flaw such as pip 22, particularly if only occasional pips are anticipated. Typically the counter 52 is reset by a signal at the end of each frame scan, as represented by the frame reset signal line 60. Counter 54 might additionally be reset by the alarming signal 55. Inasmuch as the cumulative count during each scanning frame corresponds to the size of the image on detector 38, and thus may correspond to the size of a pip 22, the count accumulated in counter 52 might alternatively be extended, as represented by broken line 57, to recorder 58 to provide a record of pip sizes during each scanning frame. In such instance, the count capacity of counter 52 might have to be increased.

In the event many pips 22 are possible, some of which may be small enough to be acceptable, it is preferable that counter 52 also be reset at the end of any line of pixels scanned on detector 38 in which no pixels in that line provided a signal on line 50. Thus, a line signal, as represented by line 62 from scanning control 45, comprises one input to comparator 54, and the other input is line 50 from slicer 48. Comparator 54 operates to pass a line reset signal, as represented by line 64, to counter 52 at the completion of each line scan in which no signal appeared on line 50 to inhibit the comparator's output. In this way, counter 52 can provide an output capable of actuating alarm 56 only if it accumulates the requisite count (i.e. 16) as a result of pixel signals 50 occurring in immediately successive line scans. This prevents two or more small, acceptable pips in one frame from being added to falsely indicate one large, unacceptable pip.

Figure 4:
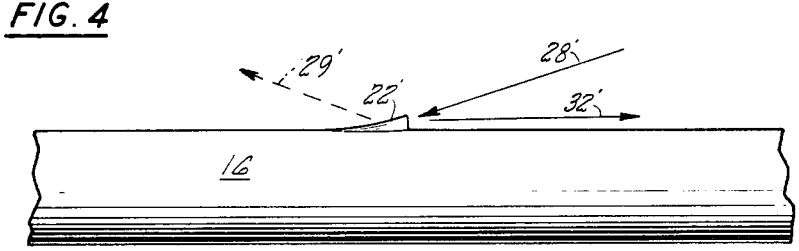
FIG. 4 is an enlarged diagrammatical view showing irradiation of a "flat-faced" flaw in accordance with an embodiment of the invention.
Figure 5:
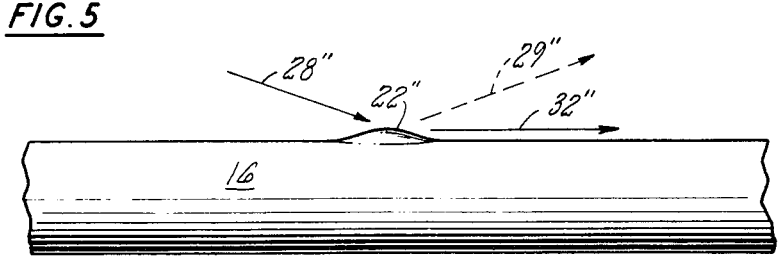
FIG. 5 is an enlarged diagrammatical view showing irradiation of a "shallow bulge" type of flaw in accordance with another embodiment of the invention.

In the event it is wished instead to detect "flat-faced" flaws or "bulges" in the surface of cable 16, the angle of incidence of the light beam with the cable surface is modified as depicted in FIGS. 4 and 5 respectively. If as depicted in FIG. 4, the flaw 22' to be detected is of a type having a "flat face" extending substantially normal to the surface of cable 16, the angle of incidence of light beam 28' must be such that it will be incident on the "flat face" of the flaw and will be scattered, as represented by line 32', toward the collecting optics. The light specularly reflected from smooth cable surface is represented by broken line 29'. The beam 28' is incident with cable 16 at an angle typically within the range of 30°-60° and from the same side of the flaw, axially, as that on which the collecting optics are located and the flat-face to be detected occurs.

Should it be desired to detect another type of flaw, such as bulge 22" in FIG. 5 in which the slope is somewhat more gradual (i.e. 10°-45°) than either of the other two aforementioned types of flaws, the angle and direction of incidence of light beam 28" would differ once again. Specifically, the incident beam 28" might be at an angle typically within the range of 30°-60° with cable 16, however, it would come at the opposite side of the flaw axially, to that on which the collecting optics are located. In this way, light specularly reflected by the smooth surface of cable 16 is at a relatively large angle, as represented by broken line 29", and is not detected by the optics. However, the light scattered by the flaw is at a shallower angle, as represented by line 32", and is collected by the optics.

Although this invention has been shown and described with respect to detailed embodiments thereof, it will be understood by those skilled in the art that various changes in form and detail thereof may be made without departing from the spirit and scope of the claimed invention. For instance, if a number of different flaw types or configurations must be detected on the same apparatus, either the angle of incidence of the light on the cable would be made adjustable or several light sources at different angles of incidence would be provided concurrently. Further, it should be understood that while using the basic optical scheme, the slicer level could be adjusted downward so as not to reject the low-level light from the normal, smooth surface, thus resulting in a cross-sectional image of the entire cable surface. Appropriate electronic processing could then be used to monitor cable surface contour, such as diameter or ellipticity.

Having thus described a typical embodiment of the invention, that which is claimed as new and desired to be secured by Letters Patent of the United States is:

1. Apparatus for detecting flaws characterized by particular changes in the normally-smooth surface of an elongated object, such as a coated cable, the object being longitudinally movable along a path relative to the apparatus, the apparatus comprising:
   means for providing a source of electromagnetic radiation and for directing said radiation at the surface of said object such that it is incident therewith in a zone extending substantially entirely around the perimeter of said object and at an angle which scatters radiation in a particular direction longitudinally of the object and within a limited angle to the object substantially only when a said flaw is present;
   a detector positioned outside the object path, said detector being responsive to electromagnetic radiation for providing an electrical signal;
   optical means for directing flaw-scattered radiation to said detector, said optical means including a mirror positioned in proximate, substantially concentric relation with said object path for deflecting, along an optical path to said detector, substantially only said electromagnetic radiation scattered by a flaw in said particular direction longitudinally of and within said limited angle to said object, said mirror including a slot therein, said slot being sized and positioned to permit said positioning of said mirror relative to said object path while said object is in said path and extending radially to a side of said object path opposite to the direction in which said radiation is reflected from the mirror towards said dectector; and wherein sad radiation incident in said zone at the surface of said object is of a relatively greater, compensating intensity in a limited angular portion of said zone aligned angularly with said mirror slot.

2. The apparatus of claim 1 further including utilization means responsive to said detector electrical signal for indicating the existence of a said flaw in said object surface.

3. The apparatus of claim 2 wherein said optical means further includes imaging means positioned intermediate said reflecting means and said detector for collecting said radiation reflected by said reflecting means and imaging said collected radiation at said detector.

4. The apparatus of claim 2 wherein said detector is an array comprising an orthogonal grid of pixels.

5. The apparatus of claim 4 wherein said detector array is a charge injection device.

6. The apparatus of claim 5 wherein said pixels of said orthogonal grid array are scanned in line-sequence, and said utilization means include logic means for resetting said counter following each line scan in which said counter fails to be incremented.

7. The apparatus of claim 4 wherein said utilization means includes a counter, said counter being conditioned to increment for each detector pixel providing an electrical signal indicative of radiation thereon above a predetermined threshold level, said counter being operative to provide an output signal indicative of a flaw when a predetermined count has been accumulated.

8. The apparatus of claim 1 wherein said source of electromagnetic radiation comprises a plurality of discrete light sources each angularly displaced from one another around the object travel path.

9. The apparatus of claim 8 wherein said discrete light sources are white light.

10. The apparatus of claim 8 wherein some of said light sources of said plurality are at a greater intensity than the others to provide said radiation of relatively greater, compensating intensity.

11. The apparatus of claim 1 wherein said object is a coated cable, said flaws are so-called pips having slopes which are steep but less than normal to the normally-smooth surface of the cable, and wherein said radiation is incident with said surface of said cable at an angle which is substantially normal thereto.

12. The apparatus of claim 1 wherein said object is a cable having a normally-smooth surface, said flaws are so-called flat-faced flaws having a flat face which is substantially normal to the surface of said cable and which substantially faces said reflecting means, and wherein said radiation is incident with said cable at an angle other than normal thereto and which scatters radiation from said flat-face of the flaw in said particular direction to said reflecting means.

13. The apparatus of claim 1 wherein said object is a cable having a normally-smooth surface, said flaws are so-called bulges having relatively shallow slopes, and wherein said radiation is incident with said cable at an angle substantially shallower than normal thereto and in a direction axially toward said reflecting means.

* * * * *